(12) United States Patent
Berland et al.

(10) Patent No.: US 8,034,990 B2
(45) Date of Patent: Oct. 11, 2011

(54) ABSORBENT ARTICLE COMPRISING HYDROPHILIC AND HYDROPHOBIC REGIONS

(75) Inventors: Carolyn Berland, Mölndal (SE); Shabira Abbas, Göteborg (SE)

(73) Assignee: SCA Hygiene Products AB, Göteborg (SE)

( * ) Notice: Subject to any disclaimer, the term of this patent is extended or adjusted under 35 U.S.C. 154(b) by 616 days.

(21) Appl. No.: 11/990,122

(22) PCT Filed: Oct. 5, 2005

(86) PCT No.: PCT/EP2005/010735
§ 371 (c)(1),
(2), (4) Date: Feb. 7, 2008

(87) PCT Pub. No.: WO2007/038964
PCT Pub. Date: Apr. 12, 2007

(65) Prior Publication Data
US 2010/0228213 A1 Sep. 9, 2010

(51) Int. Cl.
*A61F 13/15* (2006.01)
(52) U.S. Cl. ........ 604/367; 604/368; 604/370; 604/372; 604/374; 604/375; 604/377; 604/378
(58) Field of Classification Search .............. 604/367, 604/368, 370, 372, 374, 375, 377, 378
See application file for complete search history.

(56) References Cited

U.S. PATENT DOCUMENTS

| | | | |
|---|---|---|---|
| 3,998,690 A | 12/1976 | Lyness et al. | |
| 4,112,153 A | 9/1978 | Butterworth et al. | |
| 4,351,784 A | 9/1982 | Thomas et al. | |
| 4,570,629 A * | 2/1986 | Widra | 604/304 |
| 4,585,449 A | 4/1986 | Karami | |
| 4,743,494 A | 5/1988 | Komatsu et al. | |
| 4,804,378 A | 2/1989 | Shiba et al. | |
| 5,208,111 A | 5/1993 | Decher et al. | |
| 5,518,767 A | 5/1996 | Rubner et al. | |
| 5,536,573 A | 7/1996 | Rubner et al. | |
| 5,558,655 A | 9/1996 | Jezzi et al. | |
| 5,700,559 A | 12/1997 | Sheu et al. | |
| 5,807,636 A | 9/1998 | Sheu et al. | |
| 5,837,377 A | 11/1998 | Sheu et al. | |
| 5,885,753 A | 3/1999 | Crooks et al. | |
| 6,114,099 A | 9/2000 | Liu et al. | |
| 6,250,250 B1 | 6/2001 | Maishev et al. | |
| 6,258,996 B1 * | 7/2001 | Goldman | 604/368 |
| 6,451,871 B1 | 9/2002 | Winterton et al. | |
| 6,492,096 B1 | 12/2002 | Liu et al. | |
| 2003/0125683 A1 | 7/2003 | Reeves et al. | |
| 2003/0152703 A1 | 8/2003 | Hammond et al. | |
| 2003/0171729 A1 | 9/2003 | Kaun et al. | |
| 2004/0047979 A1 | 3/2004 | Qiu et al. | |
| 2004/0086709 A1 | 5/2004 | Hammond Cunningham et al. | |
| 2004/0137039 A1 | 7/2004 | Sukhishvili et al. | |
| 2004/0158214 A1 | 8/2004 | Ponomarenko et al. | |
| 2005/0069950 A1 | 3/2005 | Haynie | |

FOREIGN PATENT DOCUMENTS

| | | |
|---|---|---|
| EP | 0 272 118 | 6/1988 |
| EP | 0 997 576 | 5/2000 |
| JP | 62-261363 A | 11/1987 |
| JP | 5-285171 A | 11/1993 |
| JP | 7-136211 A | 5/1995 |
| JP | 2002-501211 A | 1/2002 |
| JP | 2004-033325 A | 2/2004 |
| JP | 2005-501758 A | 1/2005 |
| WO | WO 94/28568 | 12/1994 |
| WO | WO 95/01147 | 1/1995 |
| WO | WO 97/40793 | 11/1997 |
| WO | WO 98/24618 | 6/1998 |
| WO | WO 99/01099 | 1/1999 |
| WO | WO 99/35520 A1 | 7/1999 |
| WO | WO 00/31150 | 6/2000 |
| WO | WO 00/32702 | 6/2000 |
| WO | WO 01/15649 | 3/2001 |
| WO | WO 03/020425 A1 | 3/2003 |
| WO | WO 2004/007677 | 1/2004 |
| WO | WO 2004/025332 A1 | 3/2004 |
| WO | WO 2005/023536 | 3/2005 |
| WO | WO 2005/032512 | 4/2005 |
| WO | WO 2005/058199 | 6/2005 |

OTHER PUBLICATIONS

Notice of Opposition to a European Patent issued in corresponding Application No. 05798131.8-1219 dated Feb. 3, 2010.
International Search Report and the Written Opinion of the International Searching Authority mailed in related International Patent Application No. PCT/EP2005/010735 on Nov. 26, 2006.
Russian Official Action in RU 2008/117630, dated Feb. 26, 2009, and translation thereof.
Antipov et al., "Sustained Release Properties of Polyelectrolyte Multilayer Capsules" J. Phys. Chem. B, 2001, vol. 105, No. 12, pp. 2281-2284.
Decher et al., Multilayer Thin Films, Sequential Assembly of Nanocomposite Materials, Wiley-VCH, 2003, pp. 144-152.
Freemantle, "Polyelectrolyte Multilayers; Thin-Film Properties can be Finely Tuned Through Layer-by-Layer Assembly" Science & Technology, 2002, pp. 44-48.
Jiang et al., "Selective Deposition in Layer-by-Layer Assembly: Functional Graft Copolymers as Molecular Templates" Langmuir, 2000, vol. 16, No. 22, pp. 8501-8509.
Jiang et al., "Polymer-on-Polymer Stamping: Universal Approaches to Chemically Patterned Surfaces" Langmuir, 2002, vol. 18, No. 7, pp. 2607-2615.
Notice of Opposition dated Oct. 21, 2010, filed in corresponding European Patent No. 1,931,397.
English language translation of the Notice of Reasons for Rejection dated Oct. 26, 2010, issued by the Japanese Patent Office in corresponding Japanese Patent Application No. 2008-533873.

* cited by examiner

*Primary Examiner* — Jacqueline F Stephens
(74) *Attorney, Agent, or Firm* — Buchanan Ingersoll & Rooney PC

(57) ABSTRACT

An absorbent article such as a diaper, panty diaper, panty liner, sanitary napkin or incontinence protection, wherein at least one part of this absorbent article has a pattern of at least one hydrophilic and at least one hydrophobic region wherein the at least one hydrophilic region and/or the at least one hydrophobic region are present as a coating on the part of the absorbent article. The coated part is preferably a liquid-permeable topsheet.

26 Claims, No Drawings

ABSORBENT ARTICLE COMPRISING HYDROPHILIC AND HYDROPHOBIC REGIONS

The present disclosure relates to an absorbent article such as a diaper, panty diaper, panty liner, sanitary napkin, incontinence protection or the like wherein at least one part of this absorbent article comprises a pattern of hydrophilic and hydrophobic regions.

BACKGROUND

Absorbent articles of the present kind often comprise a liquid-pervious cover sheet topsheet that is located adjacent the wearer's body, a liquid-impervious cover sheet (backsheet) that is located distant from the wearer's body and adjacent the wearer's clothing and an absorbent layer interposed between the liquid-pervious topsheet and the liquid-impervious backsheet.

It is customary to use nonwovens and perforated film materials as topsheets. Both materials are generally made from inherently hydrophobic, synthetic polymers such as polyethylene or polypropylene.

Hydrophobic materials show almost no tendency to absorb body fluids on the surface so that after passage of body fluids and their absorption by the absorbent layer the surface develops a rather pleasant dry feel for the user. Since hydrophobic materials frequently suffer from insufficient wettability it is known to treat them with wetting agents, for instance surfactants to enhance the contact with water and liquid permeability. However, due to their capacity to bind water, hydrophilic materials tend to lead to an undesired wet feel upon discharge of body fluids.

Completely hydrophilic or hydrophobic materials are thus not capable of satisfying conflicting needs of the wearer of an absorbent article. Such materials also do not allow making use of their beneficial properties where they are mostly needed. Moreover, it is believed that neither fully hydrophobic nor fully hydrophilic materials are capable of promoting a healthy climate in the absorbent article. As healthy climate we understand in particular a low humidity environment where, despite the release of body fluids or sweat, the skin of the wearer is not prone to overhydration which is one of the most frequent causes of diaper rash.

Moreover, nanoscalar films of self-assembling polymers are known from various technical fields and have attracted considerable interest over the last years. These nanoscalar films are typically formed by the alternate deposition of monomolecular layers of two polymers having functional groups capable of interacting with each other. A great deal of these studies has been conducted with the layer-by-layer deposition (also abbreviated as LBL deposition) of cationic and anionic polymers based on the reversal of the surface charge after each deposition, one of the best-examined systems being poly(styrene sulfonate)/(polyallylamine hydrochloride) (PSS/PAH).

US 2005/0069950 A1 discloses a method for the nanofabrication of thin films, coatings and microcapsules based on suitable design of oligopeptides. Drug delivery is discussed in connection with microcapsules. Moreover, disposable diapers are mentioned as one among many possible uses for peptides designed according to this document. More concretely described are biomedical applications.

U.S. Pat. No. 5,807,636, U.S. Pat. No. 5,700,559 and U.S. Pat. No. 5,837,377 relate to a hydrophilic article for use in aqueous environments including a substrate, an ionic polymeric layer on said substrate and a disordered polyelectrolyte coating ionically bonded to said polymeric layer. Diapers and other liners are mentioned as one among many potential applications of this teaching.

WO 00/32702 describes for instance a paper or nonwoven product containing fibers, filler particles or other particles produced by the layer-by-layer deposition of two interacting polymers, preferably anionic and cationic polyelectrolytes which are typically used as dry and wet strength agents in the paper manufacture. Accordingly, this document also evaluates the tensile strength of the paper product.

Further documents relating to LBL technology are for instance: WO 2005/058199 A1; U.S. Pat. No. 5,208,111; U.S. Pat. No. 5,518,767; U.S. Pat. No. 5,536,573; U.S. Pat. No. 6,114,099; U.S. Pat. No. 6,451,871; U.S. Pat. No. 6,492,096; US 2003/152703; US 2004/0086709; WO 2005/032512; US 2004/0137039; "A. A. Antipov et al., Sustained Release Properties of Polyelectrolyte Multilayer Capsules; J. Phys. Chem. B 2001, 105, 2281-2284"; "M. Freemantle, Polyelectrolyte Multilayers; Science & Technology (2002), 44-48"; US 2004/0047979 A1; U.S. Pat. No. 5,885,753; and WO 2004/07677 A2.

There is also one document relating to multilayer construction in diapers without connection to LBL. WO 2005/023536 discloses an absorbent article comprising at least one first microlayer film region having a liquid intake function, at least one second microlayer film region having a liquid uptake and distribution function, at least one third microlayer film region having a liquid retention function, and at least one fourth microlayer film region having a liquid barrier function. These first, second, third and fourth microlayer film regions are co-extruded and assembled with each other to form the unitary micro-layered film system. However, these layers apparently have a thickness above the nm range and do not assemble themselves.

In view of the above, it is one technical object of the present disclosure to provide an absorbent article wherein the disadvantages of using fully hydrophobic or fully hydrophilic materials are avoided or alleviated.

It is one further technical object of the present disclosure to make a more efficient use of hydrophilic and hydrophobic material properties.

It is one further technical object of the present disclosure to provide an absorbent article wherein certain parts thereof can contribute in a beneficial manner to at least one relevant property such as material feel, fluid transport, healthy climate within the absorbent article or the like.

BRIEF SUMMARY

The present disclosure relates to an absorbent article such as a diaper, panty diaper, panty liner, sanitary napkin or incontinence protection wherein at least one part of said absorbent article comprises a pattern of at least one hydrophilic and at least one hydrophobic region wherein said at least one hydrophilic region and/or said at least one hydrophobic region are present as a coating on said part of the absorbent article.

In accordance with an embodiment of the present disclosure it has been found that disadvantages of fully hydrophilic or hydrophobic materials can be overcome or alleviated by providing parts of an absorbent article with a coating encompassing hydrophilic and hydrophobic regions, in particular a pattern thereof. Thereby, hydrophilic and hydrophobic material properties are utilized in an economic manner, specifically since hydrophilic and hydrophobic regions can be localized where they develop the maximum benefit to the user. The hydrophilic regions are capable of condensing and pinning water droplets from a humid atmosphere as frequently occurring in absorbent articles while the hydrophobic regions contribute to a reduction of the unpleasant wet feel often associated with fully hydrophilic materials.

DETAILED DESCRIPTION OF THE PREFERRED EMBODIMENTS

The present disclosure relates to an absorbent article such as a diaper, panty diaper, panty liner, sanitary napkin or incontinence protection, wherein at least one part thereof comprises a pattern of at least one hydrophilic and at least one hydrophobic region wherein said at least one hydrophilic region and/or said at least one hydrophobic region are present as a coating on said part of the absorbent article.

The coating may cover the entire surface of the treated part of the absorbent article or only a part thereof. Hydrophilic and hydrophobic regions are arranged in a pattern.

The term "pattern" as used herein means an intentional arrangement of elements on a surface in such a way that neither the hydrophilic nor the hydrophobic region(s) cover the entire surface. A pattern may be geometric or repetitive or both. The pattern may be regular or irregular, the former being preferred. The pattern may comprise at least one hydrophilic and more than one (e.g. at least 2, at least 5, at least 10, at least 50, etc.) hydrophobic regions or at least one hydrophobic and more than one (e.g. at least 2, at least 5, at least 10, at least 50, etc.) hydrophilic regions.

The coverage ratio of hydrophilic and hydrophobic region(s) is not specifically restricted and may for instance be 1/99 to 99/1, 5/95 to 95/5, 10/90 to 90/10 or 20/80 to 80/20.

As "hydrophobic" we preferably understand, in line with the art, a material or portion of a molecule made of a specific material that upon wetting of a smooth flat surface solely consisting of this material with water leads to sessile drop contact angles greater than 90°. Conversely, a smooth flat surface (where no effects due to surface roughness occur) that leads to contact angles of a sessile water drop of less than 90°, or where the water drop spreads spontaneously across the surface, is typically considered as "hydrophilic". The contact angle can be determined in line with TAPPI method T558PM-95 (1995) under consideration of the following:

1. The materials to be tested should be acclimatized at 23° C., 50% relative humidity over a suitable period of time (at least 4 h) prior to measurement. The measurement must be performed in a climate-controlled room (23° C., 50% relative humidity).
2. The materials to be tested should be present as a single layer of material which can be applied to a standard sample holder using double sided adhesive tapes, as for instance recommended by the manufacture.
3. Suitable parameters for the measurement are:
   a) liquid, reagent quality water
   b) a drop volume of 5 µl
   c) number of drops to be measured for averaging the results: 25
   d) in the hypothetical case where neither T558PM-95 nor the present comments address specific measurement conditions, default values as recommended by the manufacturer of the testing equipment can be used. Names of suppliers of suitable testing equipment may be found in the bound set of TAPPI test methods or may be availably from the TAPPI information resources centre. Preferred devices are manufactured by Fibro System AB, Stockholm and are marketed under the FibroDat® Trademark, such as FibroDat 1100 contact angle tester.
4. For those materials (e.g. hydrophilic, absorbent materials) where the contact angle varies with time, the measurement is conducted 0.05 sec after deposition of the drop.
5. For extremely hydrophobic surfaces the contact angle measurement may fail due to the drop beading up and rolling off the test surface. These surfaces are considered super hydrophobic.

As "absorbent article" we understand articles capable of absorbing body fluids such as urine, watery feces, female secretion or menstrual fluids. These absorbent articles include, but are not limited to diapers, panty diapers, panty liners, sanitary napkins or incontinence protection.

Such absorbent articles have a liquid-pervious cover sheet (topsheet) which during use is facing the wearer's body. They further comprise a liquid-impervious cover sheet (backsheet), for instance a plastic film, aplastic-coated nonwoven or a hydrophobic nonwoven and an absorbent layer may be enclosed between the liquid-pervious topsheet and the liquid-impervious backsheet. In some absorbent products without absorbent layer, such as specific panty liners marketed by the present applicant under various trademarks in connection with the product name "Freshness everyday", the absorbent capacity of topsheet and backsheet is sufficient to absorb small amounts of female secretion.

According to one preferred embodiment the part comprising at least one hydrophilic and at least one hydrophobic region is the liquid-permeable cover sheet.

Optionally, at least one further layer of a web or foam material is arranged between the absorbent layer and the topsheet. The at least one further layer may for instance
   be joined with the topsheet to form a multi-layer topsheet,
   aid in removing body liquids penetrating through the topsheet and/or distributing the incoming body liquids over the entire surface of the absorbent layer, as in so-called "acquisition/distribution layers", or
   belong to the core wrap of the absorbent layer.

A suitable topsheet may be manufactured from a wide range of materials such as woven and nonwoven materials (e.g. a nonwoven web of fibers), polymeric materials such as apertured plastic films, e.g. apertured formed thermoplastic films and hydroformed thermoplastic films; porous foams; reticulated foams; reticulated thermoplastic films; and thermoplastic scrims. Suitable woven and nonwoven materials can be comprised of natural fibers or from a combination of natural and synthetic fibers. Examples of suitable synthetic fibers which may comprise all or part of the topsheet include but are not limited to polyamide (e.g. nylon), acrylic (e.g. polyacrylonitrile), aromatic polyamide (e.g. aramide), polyolefin (e.g. polyethylene and polypropylene), polyester, butadiene-styrene block copolymers, natural rubber, latex, spandex (polyurethane) and combinations thereof. Synthetic fibers that contain more than one type of repeat unit can result from combining repeat units at the molecular level within each macromolecular strand (copolymer), between macromolecular strands (homopolymer blends), or combinations thereof (co-polymer blends); or they can result from combining repeat units at a higher scale level with distinct nanoscopic, microscopic, or macroscopic phases (e.g., multicomponent fibers). Each component of a multicomponent fiber can comprise a homopolymer, a copolymer, or blends thereof. Bicomponent fibers are common versions of multicomponent fibers. The two or more types of repeat units in a copolymer can be arranged randomly or in alternating blocks of each type. Blocks of different types of repeat units can jointed to one another at their respective ends (block co-polymers) or between the respective end of at least one block (graft co-polymers).

Nonwoven materials can be formed by direct extrusion processes during which the fibers and the nonwoven materials are formed at about the same point in time, or by preformed fibers which can be laid into nonwoven materials at a distinctly subsequent point in time. Exemplary direct extrusion processes include but are not limited to: spunbonding, meltblowing, solvent spinning, electrospinning and combinations thereof typically forming layers. Exemplary "laying" processes including wet laying and dry laying. Exemplary dry laying processes include but are not limited to air laying, carding and combinations thereof typically forming layers. Combinations of the above processes yield nonwovens commonly called hybrides or composites.

The fibers in a nonwoven material are typically joined to one or more adjacent fibers at some of the overlapping junctions. This includes joining fibers within each layer and joining fibers between layers when there is more than one layer. Fibers can be joined by mechanical entanglement, by chemical bond or by combinations thereof. A more detailed description of suitable topsheet materials which can be applied to the present disclosure and is incorporated by reference is found in US 2004/0158214 A1, specifically in the passage from paragraphs [0043] to [0051].

In accordance with the disclosure, it is preferred to make use of apertured plastic films (e.g. thermoplastic films) or nonwoven materials based on synthetic fibers and preferred materials are polyolefins, e.g. polyethylene or polypropylene homo- or copolymers and polymer compositions containing the same, preferably as major component by weight.

If present, the at least one further layer existing between the absorbent layer and the topsheet may be made from hydrophobic and hydrophilic web or foam materials. As "web material" we understand coherent flat fiber-based structures of paper tissue, woven or nonwoven type. The nonwoven material may have the same features as described above for topsheets.

Specifically, the at least one further layer may contribute to fluid management, for instance in the form of at least one acquisition/distribution layer. Such structures are taught for instance by U.S. Pat. No. 5,558,655, EP 0 640 330 A1, EP 0 631 768 A1 or WO 95/01147.

"Foam materials" are also well known in the art and for instance described in EP 0 878 481 A1 or EP 1 217 978 A1 in the name of the present applicant.

The absorbent layer which may be partially or totally surrounded by a core wrap may comprise any absorbent material that is generally compressible, conformable, non-irritating to the wearer's skin and capable of absorbing and retaining liquids such as urine and other body exudates.

The absorbent layer may comprise a wide variety of liquid-absorbent materials commonly used in disposable diapers and other absorbent articles such as comminuted wood pulp, which is generally referred to as air felt or fluff. Examples of other suitable absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers (such as superabsorbent fibers), absorbent gelling materials, or any other known absorbent materials or combinations of materials. Examples of some combinations of suitable absorbent materials are fluff with absorbent gelling materials and/or superabsorbent polymers, and absorbent gelling materials and superabsorbent fibers etc.

The backsheet prevents the exudates absorbed by the absorbent layer and containing with the article from soiling other external articles that may contact the absorbent article, such as bed sheets and undergarments. In preferred embodiments, the backsheet is substantially impervious to liquids (e.g., urine) and comprises a laminate of a nonwoven and a thin plastic film such as a thermoplastic film having a thickness of about 0.012 mm to about 0.051 mm. Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the absorbent article while still preventing exudates from passing through the backsheet. Exemplary breathable materials may include materials such as woven webs, nonwoven webs, composite materials such as film-coated nonwoven webs, and microporous films.

In accordance with one embodiment of the present disclosure, the hydrophobic region(s) is (are) elevated with respect to the plane of the hydrophilic region(s). Conversely, in line with this embodiment, the hydrophilic region(s) may be regarded as depression(s) with respect to the plane of hydrophobic region(s). This arrangement results for instance from the later-explained polymer-on-polymer stamping of polymers having hydrophobic molecule portions or the formation of hydrophobic pillars.

The opposite arrangement, that is hydrophilic region(s) being elevated with respect to the plane of hydrophobic regions occurs for instance with so-called "hydrophilic pillars" as also described later.

It should be understood that the expression "pattern of hydrophilic and hydrophobic regions" also includes the case of a single continuous hydrophilic region (sea) surrounding a pattern (islands) of hydrophobic regions and vice versa. Correspondingly, there are also no specific limitations regarding the shape and size of these hydrophobic and hydrophilic regions. Preferred embodiments thereof will be explained below.

According to one embodiment of the disclosure, a regular pattern is formed. According to one further aspect of this embodiment, the hydrophobic regions form elevations with respect to the plane of hydrophilic regions, or the other way round.

The hydrophilic or hydrophobic regions can adopt any suitable shape, for instance circles, squares, rectangulars, ovals or stripes. As previously mentioned, there is also no specific limitation regarding the size thereof which may for instance lie in the range of 100 $nm^2$ to 10 $cm^2$, or in line with further embodiments range from 1 $\mu m^2$ to 1 $cm^2$, 10 $\mu m^2$ to 1 $mm^2$ or 100 $\mu m^2$ to 10,000 $\mu m^2$. The latter three ranges may specifically apply to islands in a sea-island structure.

In line with one preferred embodiment of the present disclosure, at least one hydrophilic region, that is at least a part of the hydrophilic regions, preferably at least 5%, preferably at least 20%, in particular at least 50% (e.g. at least 70% or at least 90%) of all hydrophilic regions has/have a dimension below 1 mm, preferably a diameter (e.g. of circles) of less than 100 $\mu m$, more preferably a diameter of less than 20 $\mu m$, even more preferably less than 10 $\mu m$, in particular less than 5 $\mu m$. One conceivable lower limit is 100 nm. In the case of regular polygons (e.g. squares, pentagons, etc.) "diameter" is to be understood as distance from one edge to the opposite edge or corner, in the case of other shapes (e.g. stripes, etc.) as smallest axis (width). According to one alternative preferred embodiment, the above applies to the "at least one hydrophobic region".

Small dimensions of hydrophilic regions contribute to the pinning of water droplets to the hydrophilic regions. A very effective pinning has for instance been reported in US 2004/0086709 A1 (P. T. Hammond) and X. Yiang, H. Zheng, S.

Gourdin and P. T. Hammond in "Polymer-on-Polymer stamping: "Universal approaches to chemically patterned surfaces" in Langmuir 2002, 18, 2607-2615" for the condensation of water droplets on circular hydrophilic regions of a polyamine surface having a diameter of 10 µm.

In line with one embodiment of the present disclosure, the hydrophilic regions have a diameter (e.g. of circles) of 100 nm to less than 1 mm, for instance 1 µm to less than 100 µm. In the case of regular polygons (e.g. squares, pentagons, etc.) "diameter" is to be understood as distance from one edge to the opposite edge or corner, in the case of other shapes (e.g. stripes, etc.) as smallest axis (width).

According to one embodiment of the present disclosure, the hydrophilic regions form regular shapes (islands, e.g. circles) surrounded by one continuous hydrophobic region (sea) which preferably is elevated with respect to the plane of hydrophilic regions. Therein the hydrophilic regions may have the above dimensions.

Wherever the present description or the claims mention a "pattern", the "at least one hydrophilic region" or the "at least one hydrophobic region" or synonym thereof, the previous passages indicate preferred features thereof.

According to one embodiment of the present disclosure, the part of the absorbent article comprising the pattern is a perforated topsheet (e.g. plastic film or nonwoven) having a regular pattern of perforations wherein at least one part of the hydrophilic regions, preferably the majority or all hydrophilic regions are applied in register with said perforations. Preferably, the hydrophilic regions surround or encompass the perforations. In line with this embodiment, the condensation of water droplets can be localized to those areas of a cover sheet that allow the passage of body liquid to layers below the cover sheet including the absorbent layer. Correspondingly, this embodiment may not only contribute to a more efficient removal of humidity from the skin of the wearer towards the absorbent article. It may also assist in the flow of body liquids through the perforations of topsheet materials. Similarly, it is conceivable to arrange the hydrophilic regions in a multitude of stripes encompassing at least a part, preferably the majority of perforations of film-like topsheets materials to enhance and direct the flow of body liquids. Similarly, if nonwovens are used as topsheet materials, it is equally preferred to apply the hydrophilic regions to those parts showing greater porosity or, if applicable, perforations.

The hydrophilic regions are preferably formed by hydrogen donor/acceptor polymers (polymer comprising a hydrogen bond donor and/or polymer comprising a hydrogen bond acceptor) or polyelectrolyte polymers (polyanionic and/or polycationic polymer). Both systems are preferably of self-assembling type and preferably are based on alternating (typically monomolecular) layers.

The hydrophilic regions (e.g. multilayers with alternating polymers) preferably have a thickness in the nanometer scale, i.e. below 1 µm. Preferably, the hydrophilic coating has a thickness of less than 250 nm, more preferably less than 100 nm, even more preferably less than 50 nm (e.g. less than 20 nm). The measurement is conducted at a relative humidity of 50% at 20° C., after the film thickness has reached an equilibrium under these conditions.

It is preferred to provide multilayers (e.g. of hydrogen donor/acceptor or polyelectrolyte type) that are composed of two or more layers, more preferably 3 to 100 layers, in particular 4 to 50 layers (e.g. 5 to 20 layers).

Hydrogen donor/acceptor or polyelectrolyte multilayers are preferably formed in a layer-by-layer (LBL) deposition technique well known in the art of making multilayer thin films (see references mentioned under "Background of the invention" or "G. Decher and J. B. Schlenoff (ed), Multilayer Thin Films, Sequential Assembly of Nanocomposite Materials, Wiley VCH 2003", incorporated by reference).

According to one embodiment (hydrogen donor/acceptor polymers), one polymer to be used is a neutral polymer comprising a hydrogen bond donor ("hydrogen bond donor polymer") and is preferably combined with a second (different) neutral polymer comprising a hydrogen acceptor ("hydrogen bond acceptor polymer") in self-assembling alternating layers (typically monomolecular layers).

Hydrogen-bond donors are moieties that contain at least one hydrogen atom that can participate in hydrogen-bond formation and a more electronegative atom bound to the hydrogen atom. Examples of these moieties include, but are not limited to, O—H, N—H, P—H, and S—H. The moiety C—H can also be a hydrogen-bond donor if the carbon atom is bound to another atoms through a triple bond, if the carbon atom is bound through a double bond to O, or if the carbon atom is bound to at least two atoms selected from O, F, Cl, and Br.

Hydrogen-bond acceptors are moieties that contain an atom more electronegative than hydrogen that can also contain a lone pair of electrons. Examples of such atoms include, but are not limited to N, O, F, Cl, Br, I, S, and P.

The hydrogen bond donor polymer is preferably selected from polycarboxylic acid, such as polyacrylic acid (PAA) or polymethacrylic acid, a polynucleotide, a polymer of vinylnucleic acid, polyaminoacids such as polyglutamic acid and poly(E-N-carbobenzoxy-L-lysine), and polyalcohols such as poly(vinyl alcohol), and a copolymer thereof.

Preferred examples of the hydrogen bond acceptor comprise a polyether, polyketone, a polyaldehyde, a polyacrylamide, other polyamides, a polyamine, a polyurethane, a polyester, a polyphosphazene or polysaccharide or copolymer thereof. Specific examples involve polyethylene oxide, poly-1,2-dimethyoxyethylene, poly(vinylmethyl ether), poly(vinylbenzo-18-crown-6), polyvinyl butyral, poly(N-vinyl-2-pyrrolidone), polyacrylamide (PAAm), polymethacrylamide, poly(N-isopropylacrylamide), poly(4-amine)styrene, poly(cyclohexane-1,4-dimethylene terephthalate), polyhydroxy methyl acrylate, poly(bis(methylamino)phosphazene), poly(bis(methoxyethoxyethoxy)phosphazene), carboxymethyl cellulose or a copolymer thereof.

One preferred combination of hydrogen donor/acceptor polymers is PAA/PAAm.

These polymers are deposited from aqueous solutions under conditions known in the art. Hydrogen bond donor polymers comprising acidic functions such as PAA should be deposited under (typically acidic) conditions where the acidic groups exist in their non-ionized form and are therefore available for hydrogen bond formation. Similarly, hydrogen acceptor polymers should be deposited under pH conditions where the hydrogen acceptor exists in its non-ionized form. This is also to be considered when selecting a suitable combination of hydrogen bond donor and hydrogen bond acceptor polymer.

Hydrophilic coatings (regions) comprising hydrogen bond donor and/or acceptor polymers, in particular those having acidic groups (e.g. COOH) tend to dissolve at neutral and higher pH values. Depending on the location in the absorbent article and the intended function, it can thus be preferred to crosslink the same.

Crosslinking may be effected by simply heating the multilayer. A suitable temperature (e.g. 60 to 100° C.) and duration depends on the chemical nature of the treated part of the absorbent article. Thermal crosslinking is preferred if the functional groups (e.g. hydrogen donor and/or hydrogen acceptor functionality) are capable of forming bonds under release of water as in carboxy or amide groups. The crosslinking process is not restricted to bond formation between different polymers but may equally proceed within one layer having for instance carboxy groups. The thermal treatment of PAA/PAAm layers at 90° C. for 8 h (or shorter times at higher temperatures) leads for instance to the formation of anhydride and imide linkages.

Crosslinking may also be effected by chemical means. Suitable crosslinking agents can be determined by a skilled person under consideration of the functional groups (e.g. hydrogen bond donor and/or acceptor) existing in the hydrophilic coating. Polyvalent metal ions can for instance contribute to a crosslinking of carboxy groups as taught in WO 2001/015649. Divinylsulphone (DVS) is suitable to crosslink polysaccharide-based polymers such as cellulose or starch derivatives.

The hydrophilic regions may also be formed by a polyelectrolyte monolayer, preferably multilayer. These may be crosslinked, also under the conditions explained before. Multilayers are preferably deposited by layer-by-layer (LBL) deposition of polycationic and polyanionic polymers. The order of applying these polymers on a part of the absorbent article is not limited. The individual layers are typically monomolecular. As soon as the entire available surface is covered by the monomolecular layer, the repelling charges prevent the deposition of further polyelectrolyte molecules of the same type.

In line with LBL technique, the term "layer" is not to be understood in a strict sense of a material zone showing exclusively a two-dimensional extension and strict boundaries to the adjacent layer. Measurements have shown that LBL-deposited layers show a certain spread of for instance up to seven times the average layer thickness (preferably up to 4 times). In other words, a single polymer layer may penetrate into the neighbouring layers.

Nonetheless, the layering structure of these nanoscalar films and their thickness can be confirmed by various analytical techniques including UV/Vis spectroscopy, ellipsometry, QCM (Quartz crystal microbalance), X-ray reflectometry, neutron reflectometry, in situ atomic microscopy (AFM), surface force measurements and others described in "G. Decher and J. B. Schlenoff, Multilayer Thin Films". The preferred method for determining film thickness is ellipsometry.

Hydrophilic regions obtainable by layer-by-layer deposition, in particular those based on polyelectrolytes form a strong, preferably durable hydrophilic coating on hydrophobic materials, such as nonwovens or hydrophobic films or foams. Since the materials used for LBL films strongly adhere to the surface they hardly, or not at all, dissolve in body liquids. This prevents them from being entrained by body liquids during their passage to the absorbent layer. In contrast thereto, low molecular weight surfactants as typically used for hydrophilizing diaper materials dissolve in body fluids and tend to reduce surface tension of body liquids thereby lowering the wicking performance of the absorbent article. Moreover, only very small amounts are needed for film formation which ensures that important characteristics such as softness, flexibility, porosity or absorbency will not suffer to an undesired extent. A thickness below 1 µm provides the hydrophilic regions with the necessary flexibility to follow movements of the underlying substrate. The LBL technique used in the present disclosure is moreover most suitable to treat irregular surfaces such as those of fibers frequently occurring in absorbent products. An additional merit of LBL technology, specifically if non-crosslinked polyelectrolytic polymers of opposite charges are used, resides in the capacity of self-assembling polymers to form new bonds by rearrangement if bonds break, for instance due to mechanical strain. If for instance small cracks or pores arise in the LBL film as consequence of mechanical forces, these defect sites can be "repaired" after the mechanical forces cease to act and polymers with interacting functional groups are again brought in close vicinity. Further, it is advantageous that LBL technology is water-based and allows the formation of coating films without the use of potentially hazardous organic solvents.

The polymers used for LBL deposition preferably have a weight average molecular weight of at least 10,000, preferably at least 50,000, in particular at least 10,000 (as for instance determined by light scattering). Generally, higher molecular weights seem to favor LBL deposition. There is no specific upper limit regarding the molecular weight even though, in view of the desired use of a fully water-based coating technology, the polymers preferably remain water-soluble.

Weak or strong polyelectrolytes may be used in LBL deposition. In strong electrolytes such as polystyrene sulfonate, the ionisation is complete or almost complete and does not change appreciably with pH. In weak electrolytes such as polyacrylic acid, the charge density can be adjusted by changing pH. Weak polyelectrolytes typically have $pK_a$ values of about 2 to about 10 (measured at 20° C. with an aqueous solution of 1 weight % polyelectrolyte containing in addition 5 mmol NaCl). The values for PAA and PAH are for instance about 5 and 9, respectively. These polyelectrolytes may be homopolymers or copolymers wherein only a certain percentage (for instance at least 50 mol %, or less than 50 mol %) of all polymer-forming units carry the cationic or anionic group (Even though this is not always mentioned in the following for the starting materials, anionic groups in polyanionic polymers will carry a corresponding number of positive counterions, e.g. hydrogen atoms and/or metal atoms and/or onium groups (e.g. ammonium) for reasons of charge neutrality. Moreover, basic groups will be referred to as cationic even though, strictly speaking, the addition of a protic acid is required to develop the cationic charge. Accordingly, deposition must proceed under pH conditions where the anionic and the cationic charge are available for inter-layer bonding). The polyelectrolyte may also be selected from biologically active polymers (DNA, RNA, proteins, oligo- or polypeptides, enzymes, etc.), although polyelectrolyte multilayers not including these seem to be preferred.

Preferred polycationic polymers are preferably selected from homo- or copolymers of at least one monomer comprising a functional group that includes a nitrogen atom which can be protonated. They can have linear or branched structures.

Cationic polyelectrolytes can be selected from a) cationic or cationically modified polysaccharides, such as cationic starch derivatives, cellulose derivatives, pectin, galactoglucommanan, chitin, chitosan or alginate;

b) a polyallylamine homo- or copolymer, optionally comprising modifier units (suitable modifier units of the polyallylamine are known for example from WO 00/31150), in particular polyallylamine hydrochloride (PAH);

c) polyethylenemine (PEI);

d) a polyvinylamine homo- or copolymer optionally comprising modifier units, e) poly(vinylpyridine) or poly(vinylpyridinium salt) homo- or copolymer, including their N-alkyl derivatives, f) polyvinylpyrrolidone homo- or copolymer, a polydiallyldialkyl, such as poly(N,N-diallyl-N,N-di-$C_1$-$C_4$-alkyl-ammonium halide) as shown in US 2004/0047979 A1, in particular poly (N,N-diallyl-N,N-dimethylammonium chloride) (PDDA);

g) a homo- or copolymer of a quaternized di-$C_1$-$C_4$-alkyl-aminoethyl acrylate or methacrylate, for example a poly (2-hydroxy-3-methacryloylpropyl-tri-$C_1$-$C_2$-alkylammonium salt) homopolymer such as a poly(2-hydroxy-3-methacryloylpropyl trimethylammonium chloride), or a quaternized poly(2-dimethylaminoethyl methacrylate or a quaternized poly(vinylpyrrolidone-co-2-dimethylaminoethyl methacrylate)

h) a poly(vinylbenzyl-tri-$C_1$-$C_4$-alkylammonium salt), for example a poly(vinylbenzyl-tri-methylammoniumchloride), i) Polymers formed by reaction between ditertiary amines or secondary amines and dihaloalkanes, including a polymer of an aliphatic or araliphatic dihalide and an aliphatic N,N,N',N'-tetra-$C_1$-$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine, j) POLYQUAD® as disclosed in EP-A-456,467; or k) a polyaminoamide (PAMAM), for example a linear PAMAM or a PAMAM dendrimer such as an amino-terminated Starburst™ PAMAM dendrimer (Aldrich).

l) cationic acrylamide homo- or copolymers, and their modification products, such as poly(acrylamide-co-diallyldimethylammonium chloride) or glyoxal-acrylamide-resins;

m) polymers formed by polymerisation of N-(dialkylaminoalkyl)acrylamide monomers, n) condensation products between dicyandiamides, formaldehyde and ammonium salts, o) typical wet strength agents used in paper manufacture, such as urea-formaldehyde resins, melamine-formaldehyde resins, polyvinylamine, polyureide-formaldehyde resins, glyoxal-acrylamide resins and cationic materials obtained by the reaction of polyalkylene polyamines with polysaccharides such as starch and various natural gums, as well as 3-hydroxyazetidinium ion-containing resins, which are obtained by reacting nitrogen-containing compounds (e.g. ammonia, primary and secondary amine or N-containing polymers) with epichlorohydrine such as polyaminoamide-epichlorohydrine resins, polyamine-epichlorohydrine resins and aminopolymer-epichlorohydrine resins as for instance mentioned in U.S. Pat. No. 3,998,690.

Preferred polycationic polymers are cationic or cationically modified polysaccharides such as starch or cellulose derivatives, chitin, chitosan or alginate, polyallylamine homo- or copolymers, polyvinylamine homo- or copolymers or polyethylenemine.

Examples of suitable polyanionic polymers include, for example, a synthetic polymer, a biopolymer or modified biopolymer or modified biopolymer comprising carboxy, sulfo, sulfato, phosphono or phosphate groups or a mixture thereof, or a salt thereof. They can have linear or branched structures.

Examples of synthetic polyanionic polymers are: a linear polyacrylic acid (PAA), a branched polyacrylic acid, a polymethacrylic acid (PMA), a polyacrylic acid or poly-methacrylic acid copolymer, a linear or branched polycyanoacrylate, a maleic or fumaric acid copolymer, a polyamido acid, a carboxy-terminated polymer of a diamine and a di- or polycarboxylic acid (e.g., carboxy-terminated Starburst™ PAMAM dendrimers from Aldrich). Examples of a branched polyacrylic acid include a Carbophil® or Carbopol® type from Goodrich Corp. Examples of a copolymer of acrylic or methacrylic acid include a copolymerization product of an acrylic or methacrylic acid with a vinyl monomer including, for example, acrylamide, N,N-dimethyl acrylamide or N-vinylpyrrolidone.

Examples of polymers with sulfo- or sulfato groups are poly(anetholesulfonic acid), poly(vinylsulfate) (PVS), poly (vinylsulfonic acid), poly(2-acrylamido-2-methylpropanesulfonic acid) (poly-(AMPS)) or a poly(styrenesulfonic acid) (e.g. sodium poly(styrenesulfonate); PSS) and examples of polymers with phosphate or phosphonate groups involve an alkylene polyphosphate, an alkylene polyphosphonate, a carbohydrate polyphosphate or carbohydrate polyphosphonate (e.g., a teichoic acid).

Examples of polyanionic biopolymers or modified biopolymers are: hyaluronic acid, glycosaminoglycanes such as heparin or chondroitin sulfate, fucoidan, poly-aspartic acid, poly-glutamic acid, carboxymethyl cellulose, carboxymethyl dextrans, alginates, pectins, gellan, carboxyalkyl chitins, carboxymethyl chitosans, sulphated polysaccharides.

One further class of polyanionic polymers, which partially overlaps with polymers described above, are those often used as dry strength agents in paper manufacture. These include polycarboxylic acids and anhydrides such as anionic starch derivatives, (meth)acrylic acid-derived polymers and copolymers, maleic-anhydride-derived copolymers, vinyl copolymers of carboxylic acids and anionic cellulose derivatives. These can be further exemplified by polyacrylates, polymethacrylates, maleic anhydride-vinyl acetate polymers, polyvinylmethylether-maleic anhydride copolymers, methacrylic acid-acryl amide copolymers, isopropenyl acetate-maleic anhydride copolymers, itaconic acid-vinylacetate copolymers, alpha-methyl styrene-maleic anhydride copolymers, styrene-maleic anhydride copolymers, methyl methacrylate-maleic anhydride copolymers, acrylic acid-styrene copolymers, carboxymethyl cellulose, succinic half esters of cellulose, graft polymerised polyacrylate-polysaccharide copolymers, succinic half esters of starch and oxidation products of the above-listed polysaccharides. The carboxyalkylated polysaccharides include carboxymethyl cellulose (CMC), carboxymethyl hydroxycellulose (CMHEC), carboxymethyl hydroxypropylcellulose (CMHPC), carboxymethylguar (CMG), carboxymethylated locust bean gum, carboxymethyl starch and the like, and their alkali metal salts or ammonium salts.

Preferably, the polyanionic polymer is selected from homo- and copolymers of (meth)acrylic acid and anionic or anionically modified polysaccharides, such as anionic starch or cellulose derivatives such as CMC.

When selecting suitable combinations (and concentrations) of polycationic and polyanionic polymers, the interaction of potential candidates can be tested in solution prior to carrying out the deposition if both film constituents are soluble in the same solvent. When both solutions are mixed and flocculation occurs it is a good sign that multilayer fabrication will be possible. Like a chemical reaction, the precise structure of each layer depends on a set of control parameter known to a skilled person, such as concentration, pH, adsorption times, ionic strength or temperature, but in general the processing window is rather broad.

One Method for the manufacture of LBL films comprises in this order the steps of (i) contacting a substrate (e.g. diaper part to be treated) with a first aqueous solution of a polyanionic or polycationic polymer, followed by removing said first aqueous solution, (ii) optionally rinsing said part of the absorbent particle with water,
(iii) contacting said part of this absorbent article with a second aqueous solution of a polyionic polymer having the opposite charge with respect to the polymer used in step (i) followed by removing said second aqueous solution,
(iv) optionally rinsing said part of the absorbent particle with water,
(v) optionally forming at least one further alternating layer in the same manner.

In this connection, the expression "contacting" covers all known coating techniques. These include the application of the aqueous solution by means of spraying, printing and roller coating and preferably by dipping the substrate into the aqueous solution.

As "aqueous solution" we understand solutions containing water as main solvent by volume, preferably in an amount of more than 50% by volume. The aqueous solution may also contain water-miscible organic solvents, such as water-miscible alcohols (e.g. methanol or ethanol), ethers (e.g. THF) or ketones (e.g. acetone). The inclusion of organic solvents can be utilized to control the deposition of the polyelectrolyte polymer and thereby the layer thickness. Under certain conditions, mixtures of not more than 50 vol. % water and at least one water-miscible solvent may also be useful. To minimize the swelling tendency of the LBL film, it seems to be preferred to deposit the individual layers from aqueous solutions containing no further ingredients, with the possible exception of water-soluble salts such as NaCl.

There are no specific restrictions regarding the concentration of the polyelectrolyte in the first aqueous solution and the second aqueous solution. Preferably, the concentration ranges from 0.001 to 5 g/l, in particular 0.01 to 0.5 g/l.

The layer deposition can be conducted in a relatively broad temperature range although, for reasons of convenience, film formation is typically conducted at room temperature.

Analogous steps and conditions can be used for LBL depositions of hydrogen donor and acceptor polymers. It may however become necessary to conduct the optimal rinsing step with an aqueous solution having a suitable pH instead of water.

To enhance the anchorage of the LBL film to hydrophobic diaper materials such as topsheets it may be preferred to treat them with a primer and/or subject the same to a surface modification step. It is preferred to use primer materials that are known to show a good adhesion to hydrophobic materials, but simultaneously can be employed in LBL technology. Primers of this type can be appropriately selected by a skilled person and include for instance polyethyleneimine (PEI) or polyallylamine (PAH) both leading to a positive surface charge.

Preferred surface modification techniques involve a high-energy treatment. This high energy treatment includes, but is not limited to corona discharge treatment, plasma treatment (preferably in air), UV radiation, ion beam treatment, electron beam treatment and combinations thereof. Plasma or corona treatment are described for instance in WO 99/001099 and may lead to a molar oxygen/carbon ratio exceeding 0.19. Both techniques increase the hydrophilicity of nonwoven or film surfaces. Plasma-treated materials which are suitable for use as liquid-permeable topsheets are also described in U.S. Pat. No. 4,743,494 and WO 94/28568, EP 0 483 858 A1 and U.S. Pat. No. 4,351,784. Since most high-energy surface treatments, including corona and plasma treatment tend to introduce negatively charged groups into the surface, it is preferred to use polycationic polymers as first layer in the following LBL deposition.

According to one embodiment, the above high energy treatment is applied in a pattern to selected portions of the hydrophobic surface to be treated (any part of an absorbent article, in particular its topsheet). For this purpose, an electrically conducting masking material may be used which shields parts of the hydrophobic surface from the high energy treatment. One can also use more than one electrode, rotating electrodes or intermittent switching of electrodes to create patterns of areas with varying degrees of treatment coverage. One suitable technique is for instance known from U.S. Pat. No. 6,250,250 B1. In line with the present embodiment, the pattern of hydrophobic and hydrophilic regions can be generated by selective deposition (e.g. LBL deposition of hydrogen donor and/or acceptor polymers or alternating polyelectrolytes) on those portions that received the high energy treatment. This deposition technique is preferably used for generating hydrophilic regions while the hydrophobic regions correspond to those portions of the hydrophobic surface that were not modified by the high energy treatment. Regarding suitable deposition techniques and other features of the hydrophilic regions (polymer types, size and thickness, etc.) reference is made to other parts of the present application.

According to one embodiment (A) of the present disclosure, the at least one hydrophobic region is present as partial coating on a hydrophilic coating. The hydrophilic coating preferably covers the entire surface to be treated of the part (e.g. topsheet) of the absorbent article. It thus represents a continuous and coherent coating. That area or those areas of the hydrophilic coating that are not coated by the hydrophobic region(s) and thus are still exposed form the "at least one hydrophilic region". The at least one hydrophilic region has the aforementioned features.

In embodiment (A) and other embodiments of the present disclosure, the hydrophobic region(s) can be obtained by applying, to a hydrophilic coating, polymer molecules having at least one hydrophobic molecule portion and at least one functional group capable of interacting with said hydrophilic coating. This hydrophilic coating can be constituted by polymers having a hydrogen donor and/or acceptor group, or preferably a polyelectrolyte multilayer coating, as both described above.

According to one preferred embodiment, the at least one hydrophobic region is formed by at least one hydrophobic segment of a block copolymer. Preferably, the block copolymer also comprises at least one hydrophilic segment comprising a cationic or anionic group, or a hydrogen donor or acceptor group, depending on the nature of the topmost layer of the underlying hydrophilic coating. The block copolymer may be of di-block or multi-block type. The hydrophilic segment is preferably based on a polymer segment of a polycationic or polyanionic polymer as described above in connection with the formation of hydrophilic regions and LBL technology. Specifically, the hydrophilic segment is preferably obtained by polymerizing at least one ethylenically unsaturated monomer comprising a cationic or anionic group of a type constituting the already described polycationic and polyanionic polymers. To give only a few non-limiting examples, a cationic ethylenically unsaturated monomer may be selected from allylamine, vinylamine, vinylpyrridine, alkylaminoethyl (meth)acrylate, acrylamide and their derivates and salts. Non-limiting examples of a monomer carrying an anionic group are (meth)acrylic acid, maleic or fumaric acid, monomers with sulfo- or sulfato-groups, such as vinylsulfate, vinylsulfonic acid, styrene sulfonic acid, styrene sulfonate, etc.

The hydrophobic segments are preferably obtained from ethylenically unsaturated monomers carrying no polar, in particular no ionic functionality such as olefins (ethylene, propylene, etc.), aromatic vinyl compounds such as styrene, or other monomers consisting of C and H atoms.

According to one preferred embodiment the block copolymer is a polystyrene (PS)-polyacrylic acid (PAA) block copolymer, in particular di-block copolymer.

There seems to be no specific limitation regarding the molecular weight of the block copolymer. Higher molecular weight may enhance deposition but decrease solubility in conventional solvents. Weight-average molecular weights of 10,000 to 500,000 may for instance be selected. The weight ratio of hydrophobic and hydrophilic segments can be adjusted according to the degree of hydrophobicity to be achieved. Generally, it seems to be preferred to use a higher weight proportion of hydrophobic segments, in particular a ratio exceeding 5/1 or even 10/1.

One suitable block copolymer for the formation of hydrophobic regions has been described in the afore-mentioned references by Paula T. Hammond: Polystyrene-poly(acrylic acid) di-block copolymer with a PS block Mw=66500 and PAA block Mw=4500 as obtainable from Polysource, Inc, US.

Instead of the above block copolymer, a graft polymer may be used that comprises a hydrophobic main chain on which at least one hydrophilic side chain comprising a cationic or anionic group, or alternatively a hydrogen donor or acceptor group, is grafted. In these graft copolymers the main chain is preferably formed by polymerising a monomer having two or more ethylenically unsaturated units but no polar, in particular no ionic group such as butadiene. As above, the monomer preferably consists of carbon and hydrogen as constituting elements. By partial hydrogenation the number of remaining unsaturated units can be adjusted.

On the remaining unsaturated units hydrophilic side chains are grafted by polymerising an ethylenically unsaturated monomer having an anionic or cationic group, or alternatively a hydrogen donor or acceptor group. Suitable examples of anionic or cationic monomers or hydrogen donor/acceptor groups are the same as described above.

According to one aspect of embodiment (A), the at least one hydrophobic region can be applied onto the underlying hydrophilic coating by a suitable printing process, such as ink jet printing, roll printing or microcontact printing. For the treatment of small areas, microcontact printing can be used to form very precise patterns with micrometer or nanometer precision as desired. Details regarding suitable printing techniques can be found in "Multilayer thin films" edited by G. Decher and J. B. Schlenoff (ibid).

More preferably, the at least one hydrophobic region is obtainable in embodiment (A) by stamping a layer of
(i) the afore-mentioned block copolymer having at least one hydrophobic segment and at least one hydrophilic segment comprising a cationic or anionic group, or
ii) the afore-mentioned graft polymer comprising a hydrophobic main chain on which at least one hydrophilic side chain comprising a cationic or anionic group is grafted,
onto a polyelectrolyte multilayer having as an upper layer a polyelectrolyte polymer showing the opposite charge with respect to said hydrophilic segment or hydrophilic side chain.

The above technique is well known in the art as "polymer-on-polymer" stamping and is described for instance in the already cited references by Paula T. Hammond as well as US 2003/0152703 A1 (Paula T. Hammond et al.) and X. Jiang and P. T. Hammond "Selective deposition in layer-by-layer assembly: Functional graft copolymers as molecular templates", Langmuir 2000, 16, 8501-8509 and "G. Decher and J. B. Schlenoff" (ibid, pages 282 to 299 and the references cited therein).

The stamp used for applying the polymer which forms the hydrophobic regions (in the following abbreviated as "hydrophobic polymer") has a three-dimensional structured surface where the elevated areas are arranged in a pattern corresponding to the pattern of hydrophobic regions to be generated. Such stamps can be manufactured in techniques known in the art, for instance by coating a silicon master etched with the desired pattern with suitable polysiloxanes such as PDMS (Poly(dimethylsiloxane), e.g. Sylguard, 184 silicon elastomer kit, a commercial two-component curable siloxane).

The general procedure of polymer-on-polymer stamping is shown in FIG. 7 of US 2004/0086709 A1. As regards the concrete conditions for applying a hydrophobic polymer, such as PS-b-PAA block copolymer on a polyelectrolyte multilayer or single layer, reference is made to the specification of this document and in particular example 2 which is incorporated by reference. PS-b-PAA may be used to ink untreated PDMS stamps after dissolving the polymer in a suitable organic solvent such as THF. For other hydrophobic polymers a skilled person can easily determine suitable solvents and a suitable polymer concentration in this solvent. After evaporation of solvent, the stamp is preferably dried, for instance under a nitrogen stream and then brought into contact with the substrate, i.e. the diaper part carrying a hydrophilic polyelectrolyte coating.

A wide variety of stamping times may lead to the desired result ranging for instance from a second to an hour. For the concrete system examined by Paula T. Hammond stamping times of 10 to 15 min were determined to be optimal. The references by P. T. Hammond moreover show how stamping conditions including the solvent for the hydrophobic polymer to be transferred, polymer concentration, stamping time, etc. can be controlled and the stamping efficiency verified to achieve optimum results. Even though P. T. Hammond only examined the polymer-on-polymer stamping of a hydrophobic block copolymer comprising carboxylic acid functionalities on polyelectrolyte layers having as upper (or only) layer an amine-based polyelectrolyte, the interaction between hydrophobic polymers having other ionic groups and hydrophilic layers comprising in the upper (or only) layer other functionalities of opposite charge will lead to the same strong electrostatic interaction enabling transfer of the hydrophobic polymer.

Depending on the size of the hydrophobic regions to be applied, other printing techniques such as ink-jet printing or roll printing may also be used for applying the above (amphiphilic) copolymer having a hydrophobic segment or (amphiphilic) graft hydrophobic having a hydrophobic main chain.

According to one embodiment of the disclosure, one or more pillars of a further polyelectrolyte multilayer are deposited by LBL on the hydrophilic region(s) remaining after polymer-on-polymer stamping or other printing techniques. This deposition of hydrophilic "pillars" of polyelectrolyte multilayers has for instance been described in the already mentioned references by P. T. Hammond (et al), e.g. in FIG. 1 of US 2003/0152703 A1. This additional polyelectrolyte multilayer may have the same chemical composition than the underlying polyelectrolyte multilayer, although this is not essential. As to a description of these hydrophilic pillars (chemical constitution, deposition conditions, etc.) reference is made to the above explanations regarding the underlying polyelectrolyte multilayer. The total number of layers and the total thickness of polyelectrolyte multilayer pillar and underlying polyelectrolyte multilayer preferably also fulfils the previously indicated ranges. The pillars are preferably of hydrophilic islands/hydrophobic sea type.

The resulting surfaces are good for catching water droplets.

In particular very small dimensions of hydrophilic pillars are believed to be effective as follows. In line with this embodiment of the present disclosure, the hydrophilic pillars have a diameter (e.g. of circles or squares) of not more than 1 µm, preferably less than 100 nm (the lower limit may be 10 nm or less). The spacing between the pillars is not specifically limited and may for instance range from more than 1 µm, for instance more than 10 µm to several or one mm. As soon as the droplet forms, it will begin to grow by the condensation of more water vapour from the moist atmosphere of an absorbent article such as a diaper. At some point, the drop will become too large to fit on the hydrophilic pillar and then roll down to the surrounding hydrophobic surface from which it can be easily drained to the lower layer(s) of the absorbent product, such as the absorbent layer. For instance, an apertured film can be used as substrate (topsheet) so that fluid can enter the diaper even though the topsheet is hydrophobic at the base. Thus, the above-described surfaces can remove water vapour from the air thereby creating a more comfortable climate in the diaper.

According to one further embodiment, one or more pillars of a hydrophobic polymer are deposited on the hydrophobic region(s) generated by polymer-on-polymer stamping.

The resulting surfaces create a very dry feel against the skin.

The afore-mentioned embodiments of the disclosure are particularly suitable for sheet- or film-like parts of an absorbent article having relatively smooth surfaces such as perforated films where polymer-on-polymer stamping can be most effectively used.

According to embodiment (B) of the present disclosure the coating carried by the part (e.g. topsheet) of the absorbent article is solely formed by the at least one hydrophobic or the at least hydrophilic region. Accordingly, the coating does not cover the entire surface of said part and forms itself a pattern. In this connection the word "coating" does not encompass optional primer treatments of said part of an absorbent article.

According to the first aspect of embodiment (B), at least one hydrophilic region forms a pattern on a hydrophobic part of the absorbent article.

In line with this aspect of embodiment (B), it is preferred to subject any hydrophobic part of the absorbent article, for instance topsheets made from hydrophobic materials to the afore-mentioned high energy surface treatment prior to coating with at least one hydrophilic region. This high energy surface treatment is intended to increase the anchorage of the hydrophilic region (partial coating) on the underlying hydrophobic part of the absorbent article.

Basically, two techniques are conceivable to conduct the high energy surface treatment such as corona discharge or plasma treatment. Firstly, the high energy surface treatment is applied under conditions leading to the temporary generation of (negative) charges on the hydrophobic surface. Then, printing techniques, as described before, are utilized for applying a pattern of at least one hydrophilic region on the charged surface. For instance microcontact printing, in particular polymer-on-polymer stamping can also be used for generating a pattern of at least one hydrophilic region, in particular a polyelectrolyte pattern. As to details, reference can again be made to "Multilayer thin films" edited by G. Decher and J. B. Schlenoff (Ibid), for instance the passage starting on page 146 and the references cited in this passage. In those areas of the hydrophobic surface which carry no hydrophilic region(s) the negative charges tend to dissipate after a while whereby the surface partially or fully returns to its original hydrophobic state.

Alternatively, the high energy surface treatment is applied in a pattern as described before. Then, it is not necessary to apply specific printing processes. Hydrophilic regions can be selectively bound to those areas that received the high energy treatment. Moreover, it is possible to pre-treat the surface of the hydrophobic part (e.g. topsheet) by applying a pattern of a suitable primer such as PEI or PAH.

Regardless of which pretreatment is used, it is preferred that the at least one hydrophilic region is formed by a polyelectrolyte layer, in particular polyelectrolyte multilayer. This polyelectrolyte multilayer is preferably obtainable by layer-by-layer (LBL) deposition of at least one polycationic and polyanionic polymer. In this connection, reference can be made to the previous description of LBL deposition regarding suitable deposition conditions, polyelectrolytes to be used and other features thereof.

The previous paragraph described techniques for selectively applying a pattern of at least one hydrophilic region on hydrophobic parts of an absorbent article. Selective dissolution of a continuous hydrophilic coating may also be used to achieve the same purpose. This will be described in more detail in the following.

Accordingly, any hydrophobic part of an absorbent article, for instance a topsheet made from hydrophobic material is optionally subjected to a high energy surface treatment or primer treatment as described before. Then, a continuous hydrophilic coating is formed, preferably by LBL deposition of hydrogen donor and/or acceptor polymers or polyelectrolytes, that is polyanionic and/or polycationic polymers. This hydrophilic coating can be formed under the previously described conditions and preferably shows the afore-mentioned features. Preferably, the hydrophilic coating comprises any of the hydrogen acceptor polymers described before and a hydrogen donor polymer that comprises an acidic group. Such hydrogen donor polymers can be selected under the previously indicated polymer classes, the use of polyacrylic acid and polymethacrylic acid being preferred. These hydrogen donor and hydrogen acceptor polymers are deposited under acidic conditions where the hydrogen donor groups exist in their nonionized form and are therefore available for hydrogen bond formation. Using PAA and PAAm, the pH of both the dipping and rinsing solution is for instance adjusted to 3.0 with aqueous HCl and no salt is added to the solutions.

In the following step a pattern of selected regions is treated by contacting the hydrophilic coating with water or an aqueous solution, preferably an aqueous buffered solution that has a higher pH than the pH under which deposition proceeded (difference preferably at least 1.5 pH units, preferably at least three pH units). Preferred pH values of the aqueous solution range for instance from 4.5 to 9, in particular 6 to 8. PAA/PAAm multilayers dissolve for instance quickly in pH 4.5 or higher aqueous solutions, or even faster in pH 7.0 phosphate buffer solutions. Ink-jet printing is suitable for precisely applying this pattern of an aqueous, in particular aqueous buffered solution. Details can be found in "Multilayer thin films" edited by G. Decher and J. B. Schlenoff (Ibid), for instance in the passage starting on page 148, and references cited therein. FIG. 5.11 on page 150 of this book further schematically describes this subtractive ink-jet printing process.

After ink-jet printing the hydrophilic coating is dried and crosslinked, preferably by the afore-mentioned thermal crosslinking process. Since the aqueous (buffered) solution ionises hydrogen donor groups, such as carboxy groups, only the remaining (unprinted) regions remain intact and are prone to crosslinking.

In the following step the noncrosslinked (i.e. printed) regions of the coating can be washed off with water thereby newly exposing the hydrophobic surface of the coated part (e.g. topsheet) of the absorbent article.

Regarding suitable hydrophobic materials, reference can be made to the previous description of topsheet materials, including polymer classes disclosed in connection with synthetic fibers. Preferred hydrophobic materials are polyolefins, such as polyethylene or polypropylene homo- or copolymers and polymer compositions containing the same, preferably as major component by weight.

According to the second aspect of embodiment (B), at least one hydrophobic region forms a pattern on a hydrophilic part of the absorbent article.

The hydrophilic part may for instance be a topsheet or a layer between the absorbent layer and the topsheet ("at least one further layer") made from naturally occurring fibers, in particular cellulosic fibers as present in cellulosic pulp. Alternatively, hydrophobic materials as disclosed above in connection with topsheets are subjected to a hydrophilisation treatment before a pattern of hydrophobic regions is applied. Suitable hydrophilisation treatments involve the application of surfactants or the already mentioned primer treatment. The at least one hydrophobic region generating the pattern is preferably applied by one of the afore-mentioned printing techniques. The at least one hydrophobic region is preferably formed by at least on hydrophobic segment of a block copolymer or a graft polymer comprising a hydrophobic main chain. For this purpose, the same block copolymers or graft polymers described before in connection with polymer-on-polymer stamping can be used.

It should be understood that wherever features (materials, conditions, uses, etc.) are referred to as preferred in the present specification, the disclosure of the present application also extends to a combination of at least two of these features as long as these do not contradict each other.

The present disclosure is now illustrated by more preferred embodiments. These embodiments reflect a combination of features that can be advantageously used to practice the disclosure.

Embodiment 1

A topsheet (e.g. polyethylene nonwoven or apertured film) or a similar part of an absorbent article such as a diaper is optionally corona- or plasma-treated to generate temporary negative charges. This treatment can be applied over the entire topsheet or over a portion of the topsheet (wetting zone, middle third of topsheet, etc.). The optionally treated polyethylene nonwoven or film is immersed in PEI and PAA solutions (or sprayed, printed, roll coated therewith) to form alternate self-assembled layers of PEI (polyethylenimine) and PAA (polyacrylic acid). At least one, preferably at lest two layers are applied. A rinsing stage can be used between coating stages to remove excess polymer, if needed. Alternatively, polyallylamine hydrochloride (PAH) or any other amine-based polymer is used instead of PEI. The coating process is terminated with the deposition of a PEI or polyamine layer.

Then, a pattern of hydrophobic regions is generated by polymer-on-polymer stamping of a suitable block copolymer, for example PAA-PS onto the PEI or polyamino surface. The resulting surface can pin water droplets in the hydrophilic area.

Embodiment 2

On the patterned surface generated in embodiment 1 hydrophilic pillars can be formed by further deposition of a polyelectrolyte multilayer on the hydrophilic regions. For this purpose, the same polyanionic and polycationic polymers as described before in connection with LBL technology and the corresponding deposition conditions can be used.

The resulting surfaces are good for catching water droplets which will roll down to the surface when they become sufficiently large. Moreover, these surfaces can remove water vapour from the air thereby creating a more comfortable climate in the diaper. In this case an apertured film may be used as substrate so that fluid can enter the diaper even though the topsheet is hydrophobic at the base.

Embodiment 3

A hydrophobic substrate, for instance a polyolefin-based nonwoven or a perforated film as used for topsheets is optionally subjected to a high energy surface treatment (e.g. corona discharge) to create (negative) surface charges on the entire surface. Preferably, conditions are chosen for the high energy treatment that lead to the temporary formation of negative charges.

As positively charged polymer, preferably one of the afore-mentioned polycationic polymers is applied by a printing process in a desired pattern. The preferred printing process is inkjet printing for fine pattern in view of the high precision to be achieved whereas other printing processes such as roll printing can be used for larger patterns. To generate very small patterns, microcontact printing (polymer-on-polymer stamping) can be used. After deposition of the polycationic polymer from an aqueous solution thereof, the substrate is optionally rinsed with water.

If desired, a second polymer layer of opposite charge, that is a polyanionic polymer, is applied by dipping the substrate into an aqueous solution thereof, or by spraying, roll-coating, etc. The polyanionic polymer will adhere only to the printed regions.

The resulting substrate carrying a polyelectrolyte bilayer pattern is optionally again rinsed with water. This deposition cycle can be repeated to generate further layers.

If further deposition cycles are conducted it is preferred to await dissipation of negative charges on the hydrophobic substrate before the substrate is newly contacted with polycationic polymer solutions. Under this precondition, the polycationic polymer will show the maximum adhesion to the multilayer pattern having as topmost layer a polyanionic polymer.

Other hydrophobic substrates such as polyolefin-based perfluorated film materials can be treated in the same manner.

Embodiment 4

Selective Dissolution and Crosslinking

A hydrophobic substrate as exemplified in embodiment 3 is optionally subjected to a high energy surface treatment such as corona discharge treatment to create negative surface charges.

The substrate is dipped one after another into aqueous solutions of poly(acrylic)acid and poly(acrylamide), which were adjusted to pH 3 with hydrochloric acid, to generate alternating layers of PAA and PAAm. The layers may be optionally rinsed with a dilute solution of hydrochloric acid (pH 3.0) to remove excess polymer.

After the desired number of layers has been applied, a pattern of selected regions to be removed is contacted with an aqueous solution/water having a pH above 3.0. Preferably, neutral water or a buffer (e.g. phosphate buffer) having a pH of 7 is used. In principle, depending on the size of the regions to be removed, contact with the aqueous solution/water and removal may be conducted in one step, for instance by using focused water jet, prior to the following crosslinking step.

Generally, it is however preferred to subject the coating first to drying and crosslinking. Crosslinking can be thermally effected by heating the coated substrate to 90° C. for at least 8 h. During this crosslinking step only those regions of the coating that were not contacted with water are capable of undergoing crosslinking chemical reactions, such as the formation of anhydride or imide bonds.

Subsequently, the coating is washed with water to remove the non-crosslinked regions that were previously contacted with water thereby exposing the underlying hydrophobic substrate. In this manner, a pattern of at least one hydrophilic and hydrophobic region can be formed. As regards details of this process, reference can be made to "Multilayer thin films", edited by G. Decher and J. B. Schlenoff (Ibid) and the references cited therein.

It should be noted that, despite the hydrophilising high energy surface treatment, the generated (negative) charges on the surface tend to dissipate upon aging so that the surface will regain or approach its original hydrophobic state.

Embodiment 5

If the treated substrate (such as hydrophilic nonwoven or tissue paper) is originally hydrophilic a high energy surface treatment is not required. Then, a hydrophilic/hydrophobic pattern can be achieved by selectively applying in a pattern a final layer of a suitable block polymer having at least one hydrophobic region or graft polymer comprising a hydrophobic main chain onto a continuous polyelectrolyte multilayer coating. The hydrophilic polymer can be exemplified by polymers as discussed in connection with polymer-on-polymer stamping. It preferably comprises a functional group, for instance a cationic or anionic group that selectively bonds to the upper polyelectrolyte polymer layer showing the opposite charge.

Embodiment 6

Patterned Corona Treatment

An (optionally perforated) polyethylene-based nonwoven or a perforated film, preferably of the type as used for topsheet manufacture, is subjected to a patterned high energy surface treatment, such as corona discharge or plasma treatment to create a pattern of negative charges on the hydrophobic surface. The pattern is preferably applied in register with the perforations in a manner that the treated areas encompass or surround the perforations.

The resulting nonwoven or film is then immersed alternately into aqueous solutions of a suitable polycationic polymer, such as polyacrylic acid (PAA) and polyanionic polymer, such as poly(allylamine hydrochloride) (PAH) to deposit at least two coating layers. After each dipping step, the nonwoven or film is optionally rinsed with water. This deposition cycle can be repeated to form the desired number of layers. After the final deposition step, the nonwoven or film is again optionally rinsed with water and then dried.

The invention claimed is:

1. An absorbent article wherein at least one part of this absorbent article comprises a pattern of at least one hydrophilic and at least one hydrophobic region wherein said at least one hydrophilic region and/or said at least one hydrophobic region are present as a coating on said part of the absorbent article, and wherein the at least one hydrophilic region is formed by a polyelectrolyte layer.

2. The absorbent article according to claim 1 wherein said part is a liquid-permeable cover sheet.

3. The absorbent article according to claim 2 wherein a part of the liquid-permeable cover sheet is a perforated plastic film or nonwoven having a regular pattern of perforations and the hydrophilic regions are applied in register with said perforations.

4. The absorbent article according to claim 1 wherein said pattern is regular.

5. The absorbent article according to claim 1 wherein the at least one hydrophobic region is elevated with respect to the plane of the at least one hydrophilic region.

6. The absorbent article according to claim 1 wherein the hydrophilic regions are surrounded by one continuous hydrophobic region.

7. The absorbent article according to claim 6, wherein the hydrophilic regions have the form of circles.

8. The absorbent article according to claim 1 wherein at least a part of the hydrophilic or hydrophobic regions have a diameter of less than 100 µm.

9. The absorbent article according to claim 1 wherein the polyelectrolyte layer is a polyelectrolyte multilayer.

10. The absorbent article according to claim 9 wherein the polyelectrolyte multilayer obtained by layer-by-layer (LBL) deposition of at least one polycationic and at least one polyanionic polymer.

11. The absorbent article according to claim 10 wherein the polycationic polymer is selected from cationic or cationically modified polysaccarides, polyallylamine homo- or copolymers, polyvinylamines homo- or copolymers and polyethylenemine.

12. The absorbent article according to claim 10, wherein the polyanionic polymer is selected from (meth)acrylic acid homo- or copolymers and anionic or anionically modified polysaccaride derivatives.

13. The absorbent article according to claim 9 wherein the polymer(s) constituting the hydrophilic region(s) are crosslinked.

14. The absorbent article according to claim 1 wherein the at least one hydrophilic region is formed by at least one polymer comprising a hydrogen donor group and/or at least one polymer comprising a hydrogen acceptor group.

15. The absorbent article according to claim 1 wherein the at least one hydrophobic region is present as partial coating on a hydrophilic coating carried by said part of the absorbent article and the area(s) of the hydrophilic coating that is (are) not coated by the at least one hydrophobic region form the at least one hydrophilic region.

16. The absorbent article according to claim 15 wherein one or more pillars of a polyelectrolyte multilayer are deposited on the at least one hydrophilic region.

17. The absorbent article according to claim 1 wherein the at least one hydrophobic region is formed by at least one hydrophobic segment of a block copolymer or a graft polymer comprising a hydrophobic main chain.

18. The absorbent article according to claim 1 wherein the pattern of at least one hydrophilic and at least one hydrophobic regions is obtained by stamping a layer of (i) a block copolymer having at least one hydrophobic segment and at least one hydrophilic segment comprising a cationic or anionic group or (ii) a graft polymer comprising a hydrophobic main chain, on which at least one hydrophilic side chain comprising a cationic or anionic group is grafted, onto a polyelectrolyte layer.

19. The absorbent article according to claim 1 wherein the at least one hydrophilic region forms a pattern on a hydrophobic part of the absorbent article.

20. The absorbent article according to claim 19 wherein the hydrophobic part of the absorbent article was subjected to a high energy surface treatment prior to the coating with at least one hydrophilic region.

21. The absorbent article according to claim 20, wherein this high energy treatment was applied in the form of a pattern.

22. The absorbent article according to claim 20 wherein the at least one hydrophilic region is formed by alternating layers of one neutral polymer having a hydrogen donor group and one neutral polymer having a hydrogen acceptor group.

23. The absorbent article according to claim 20 wherein the at least one hydrophilic region comprises crosslinked hydrophilic polymers.

24. The absorbent article according to claim 1 wherein the at least one hydrophobic region forms a pattern on a hydrophilic part of the absorbent article.

25. A liquid-permeable cover sheet for an absorbent article wherein this cover sheet comprises a pattern of at least one hydrophilic and at least one hydrophobic region wherein said at least one hydrophilic region and/or said at least one hydrophobic region are present as a coating on said cover sheet, and wherein the at least one hydrophilic region is formed by a polyelectrolyte layer.

26. The cover sheet according to claim 25, wherein the pattern is regular.

* * * * *